US009974500B2

(12) United States Patent
Khamaisi

(10) Patent No.: US 9,974,500 B2
(45) Date of Patent: May 22, 2018

(54) SYSTEMS AND METHODS FOR OPEN IMAGING

(71) Applicant: GE Medical Systems Israel, Ltd., Tirat Hacarmel (IL)

(72) Inventor: Raed Khamaisi, Tirat Hacarmel (IL)

(73) Assignee: GE Medical Systems Israel, Ltd., Tirat Hacarmel (IL)

( * ) Notice: Subject to any disclaimer, the term of this patent is extended or adjusted under 35 U.S.C. 154(b) by 416 days.

(21) Appl. No.: 14/329,438

(22) Filed: Jul. 11, 2014

(65) Prior Publication Data
US 2016/0007940 A1    Jan. 14, 2016

(51) Int. Cl.
| | | |
|---|---|---|
| A61B 5/05 | (2006.01) | |
| A61B 6/00 | (2006.01) | |
| A61B 6/03 | (2006.01) | |
| A61B 6/04 | (2006.01) | |
| A61B 6/12 | (2006.01) | |
| A61B 10/02 | (2006.01) | |
| A61B 90/11 | (2016.01) | |

(52) U.S. Cl.
CPC ............ *A61B 6/44* (2013.01); *A61B 6/037* (2013.01); *A61B 6/0414* (2013.01); *A61B 6/12* (2013.01); *A61B 6/4266* (2013.01); *A61B 6/502* (2013.01); *A61B 10/0233* (2013.01); *A61B 90/11* (2016.02)

(58) Field of Classification Search
USPC ........................................................ 600/424
See application file for complete search history.

(56) References Cited

U.S. PATENT DOCUMENTS

| | | | |
|---|---|---|---|
| 5,252,830 A | | 10/1993 | Weinberg |
| 5,825,031 A | * | 10/1998 | Wong ................... G01T 1/164 250/363.03 |
| 5,938,604 A | | 8/1999 | Wagner et al. |
| 5,961,457 A | | 10/1999 | Raylman et al. |

(Continued)

FOREIGN PATENT DOCUMENTS

WO    2013063133 A1    5/2013

OTHER PUBLICATIONS

Amanda L. Weinmann, et al., Design of Optimal Collimation for Dedicated Molecular Breast Imaging Systems, Med. Phys. 36 (3), Feb. 19, 2009, pp. 845-856.

(Continued)

*Primary Examiner* — Joel F Brutus
(74) *Attorney, Agent, or Firm* — Dean D. Small; The Small Patent Law Group, LLC

(57) ABSTRACT

A molecular breast imaging (MBI) unit includes a housing, a first detector unit, and a second detector unit. The housing is configured to be positioned in an imaging position for imaging an object. The first detector unit includes a first nuclear medicine (NM) imaging detector secured in the housing. The first detector unit is configured to acquire first imaging information of the object when the housing is in the imaging position. The second detector unit includes a second NM imaging detector secured in the housing. The second detector unit is configured to acquire second imaging information of the object when the housing is in the imaging position. The housing includes an opening disposed between the first and second detector units. The opening is configured to allow access by a biopsy assembly to the object with the housing in the imaging position.

21 Claims, 10 Drawing Sheets

(56) References Cited

U.S. PATENT DOCUMENTS

| | | | |
|---|---|---|---|
| 6,490,467 | B1 | 12/2002 | Bucholz et al. |
| 7,102,134 | B2 | 9/2006 | Weinberg |
| 7,711,409 | B2 | 5/2010 | Keppel et al. |
| 2002/0057758 | A1* | 5/2002 | Stark .................. A61B 6/0414 378/37 |
| 2004/0054248 | A1* | 3/2004 | Kimchy ................ A61B 5/055 600/3 |
| 2006/0224149 | A1 | 10/2006 | Hillely |
| 2008/0084961 | A1 | 4/2008 | Keppel et al. |
| 2008/0086059 | A1 | 4/2008 | Keppel et al. |
| 2009/0163830 | A1 | 6/2009 | Hibner et al. |
| 2010/0016713 | A1 | 1/2010 | Welch |
| 2010/0019918 | A1 | 1/2010 | Avital et al. |
| 2010/0183213 | A1 | 7/2010 | Keppel et al. |
| 2010/0261997 | A1 | 10/2010 | Ren et al. |
| 2010/0329419 | A1 | 12/2010 | Blevis |
| 2011/0216880 | A1 | 9/2011 | Blevis |
| 2011/0268339 | A1 | 11/2011 | Volokh et al. |
| 2012/0108948 | A1* | 5/2012 | Jansen .................. A61B 6/037 600/411 |
| 2013/0131509 | A1 | 5/2013 | Rafaeli et al. |
| 2013/0223590 | A1 | 8/2013 | Rafaeli et al. |
| 2013/0320234 | A1 | 12/2013 | Volokh et al. |
| 2013/0345550 | A1 | 12/2013 | Rafaeli et al. |

OTHER PUBLICATIONS http://www.surgiceye.com/en/download/senses_flyer_eu_se6001-eu03_email.pdf, (5) pgs., Nov. 21, 2012.

Kambiz Rahbar, et al., Intraoperative 3-D Mapping of Parathyroid Adenoma Using Freehand Spect, http://www.springerlink.com/content/0612m7575g01k73n/, (4) pgs., Sep. 27, 2012.

http://www.naviscan.com/images/stories/Naviscan_CE_Mark_Press_Release_Sept_8_BX_revised9.7.11.pdf, (1) pg., Sep. 8, 2011.

Product Overview, http://www.naviscan.com/products, (1) pg., Nov. 21, 2012.

Mayo Clinic—Molecular Breast Imaging: A Better Way to Spot Tumors in Dense Tissue, http://www.mayoclinic.org/news2009-mchi/5203.html, (1) pg., Mar. 10, 2009.

Gamma Medica (Index.html): http://www.gammamedica.com/, (2) pgs., Nov. 21, 2012.

Products & Services / Dilon Diagnostics, http://dilon.com/pages/products_and_services/4.php, (1) pg., Nov. 21, 2012.

Gamma Medica-Ideas Introduces New Tri-Modality FLEX Triumph™ Pre-Clinical Imaging System, http://www.gammamedica.com/pr_060830.html, (2) pgs., Aug. 30, 2006.

Thomas Wendler, et al., First demonstation of 3-D lymphatic mapping in breast cancer using freehand SPECT, Eur J Nucl Med Mol Imaging (2010) 37:1452-1461.

http://www.naviscan.com/images/stories/Naviscan_CE_Mark_Press_Release_Sept_8_BX_revised_9.7.11.pdf.

http://www.mayoclinic.org/news2009-mchi/5203.html.

International Search Report and Written Opinion issued in connection with corresponding PCT Application No. PCT/IB2015/001366 dated Dec. 2, 2015.

* cited by examiner

SYSTEMS AND METHODS FOR OPEN IMAGING

BACKGROUND OF THE INVENTION

The subject matter disclosed herein relates generally to systems and methods for nuclear medicine (NM) imaging, for example molecular breast imaging (MBI).

Various imaging techniques may be utilized to identify structures or aspects, such as lesions, within a portion of a patient. After a lesion is identified, it may be desirable to perform a biopsy to further analyze or diagnose the lesion. Conventionally, after identification of a lesion, the biopsy may be performed at a separate location and/or time (e.g., a separate visit to a practitioner's office, and/or using separate equipment). In some approaches, a grid plate having grid of holes arranged in rows and columns may be employed, with a biopsy needle inserted through a predetermined hole of the grid. Conventional approaches, however, may require the use of fiducial markers, transformation of coordinates, and/or other techniques to locate a lesion for biopsy that result in issues regarding reliability and/or accuracy of positioning a biopsy needle.

BRIEF DESCRIPTION OF THE INVENTION

In one embodiment, a molecular breast imaging (MBI) unit includes a housing, a first detector unit, and a second detector unit. The housing is configured to be positioned in an imaging position for imaging an object. The first detector unit includes a first nuclear medicine (NM) imaging detector secured in the housing. The first detector unit is configured to acquire first imaging information of the object when the housing is in the imaging position. The second detector unit includes a second NM imaging detector secured in the housing. The second detector unit is configured to acquire second imaging information of the object when the housing is in the imaging position. The housing includes an opening disposed between the first and second detector units. The opening is configured to allow access by a biopsy assembly to the object with the housing in the imaging position.

In another embodiment, an imaging system includes a bottom detector unit, an upper detector unit, an imaging unit. The bottom detector unit is mounted to a support structure. The upper detector unit is mounted to the support structure, and is movable from an upper detector imaging position to an upper detector clearance position. The imaging unit is configured to be mounted to the support structure in an imaging position when the upper detector unit is in the upper detector clearance position. The imaging unit includes a housing, a first detector unit, and a second detector unit. The first detector unit includes a first nuclear medicine (NM) imaging detector secured in the housing, and is configured to acquire first imaging information of the object when the imaging unit is in the imaging position. The second detector unit includes a second NM imaging detector secured in the housing, and is configured to acquire second imaging information of the object when the imaging unit is in the imaging position. The housing includes an opening disposed between the first and second detector units. The opening is configured to allow access to the object with the housing in the imaging position.

In another embodiment, a method includes determining, with one or more detector units, a location of a region of interest within an object with respect to a first and second dimension. The method also includes positioning an imaging unit in an imaging position proximate the object. The imaging unit comprises a housing, a first detector unit, and a second detector unit. The housing comprises an opening disposed between the first and second detector units. The opening is configured to allow access by a biopsy assembly to the object when the imaging unit is in the imaging position. A central axis of the opening is aligned with the region of interest when the imaging unit is in the imaging position. The method further includes determining, using imaging information from the first and second detector units, a depth of the region of interest from a surface of the imaged object, the depth extending from a plane defined by the first and second dimensions.

DETAILED DESCRIPTION OF THE INVENTION

Figure 1:
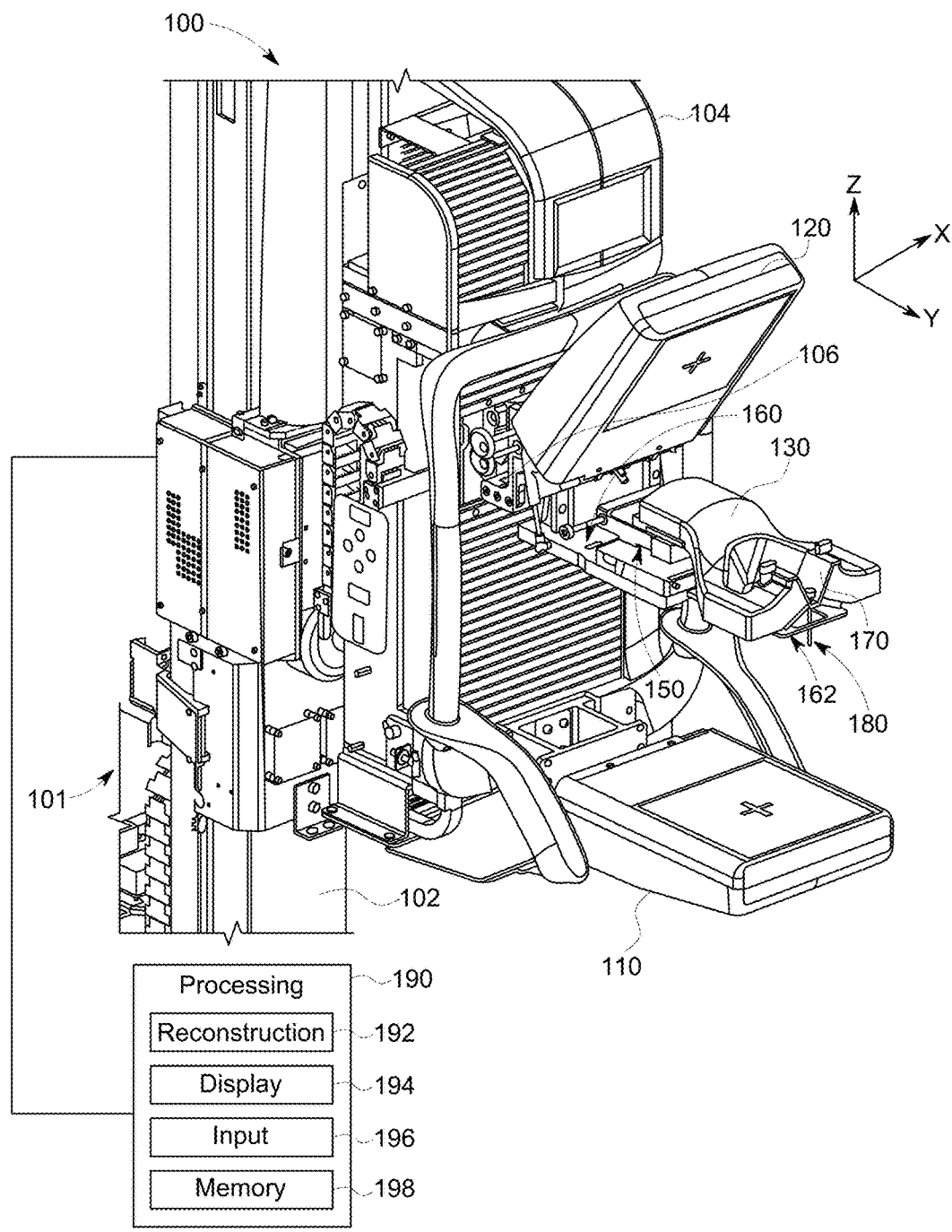
FIG. 1 is a schematic diagram illustrating an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. It may be noted that, for example, a "processor" or "controller" as used herein may be include plural processors or controllers configured to cooperate together, and is not necessarily limited to a single "processor" or "controller." A module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for identifying, locating, and/or performing a biopsy on a lesion or other aspect of a portion of an object such as a human patient, for example a lesion of a breast. For example, various embodiments provide a molecular breast imaging (MBI) biopsy attachment (e.g., an imaging unit configured for imaging during performance of a biopsy) having an open design (e.g., having an opening proximate a detection unit and/or between detection units) providing access to tissue of an object being imaged. The access allows viewing of the tissue before and/or after insertion of a biopsy needle by a practitioner. In various embodiments, by allowing insertion of the biopsy needle or related equipment between detection units of the imaging unit, the interior or volume being imaged of the patient may be viewed (e.g., on a screen) by the practitioner, for example, to one or more of determine the depth of the lesion, confirm the location of the lesion, view the insertion of a biopsy needle, or view the position of the biopsy needle during the performance of the biopsy and/or preparation for the biopsy.

The open design of various embodiments also provides convenient access for making an incision in the skin, inserting a biopsy needle, and performing a biopsy (e.g., extracting material from an identified lesion) with the imaging unit in place and being used to provide images of the region of interest. In contrast to use of a pressure plate with a grid of holes, a guide plate with a relatively low number of holes (e.g., a single hole or two holes, among others) may be employed. For example, the guide plate may include a first hole configured for use for most biopsies, and a second hole positioned proximate an edge of the plate that may be used for lesions that are near or close to the chest wall. A hole of the guide plate may be placed above (e.g., directly above) the location of the lesion. For example, the location of the lesion in two dimensions (e.g., an x dimension and a y dimension) may be determined previous to the positioning of the imaging unit using one or more main detection units. With the x-y location known, the hole of the guide plate (or a corresponding portion of the imaging unit) may be positioned using manual adjustment devices, such as knobs, or may be automatically positioned by a processing unit. With the open design imaging unit positioned as desired, the depth of the lesion may be determined using detection units of the open design imaging unit (e.g., detection units on either side of an opening of the open design imaging unit) that are slanted or angled with respect to the x-y plane. A detection unit may be understood as slanted or angled with respect to a plane when a line of sight of the detector unit is not substantially parallel to and not substantially perpendicular to the plane (e.g., the plane in which the location of the lesion has already been determined). In various embodiments, a biopsy tool (e.g., biopsy needle) may be directly attached or coupled to the MBI biopsy attachment or imaging device (e.g., via insertion through a guide hole of a guide plate attached to the housing), therefore eliminating the use of fiducial markers or transformation of coordinates. In various embodiments, a sterile plate and/or other sterile member may be positioned proximate the opening of the imaging unit.

Various embodiments provide improved imaging. Various embodiments provide for improved performance of biopsies. A technical effect of at least one embodiment includes improved reliability and/or accuracy of positioning a biopsy needle. A technical effect of at least one embodiment includes reduction in the time and/or number of office visits required for identification of a lesion and performing a biopsy of the lesion.

FIG. 1 illustrates an imaging system 100 in accordance with an embodiment. The imaging system 100 may be configured, for example, to image an object (e.g., a breast) for location (e.g., a location within a first plane such as an x-y plane) of a target or region of interest within the object (e.g., a lesion), to confirm the location and/or determine a depth (e.g., a location outside of the first plane, such as in a direction normal or perpendicular to the first plane) of the target or region of interest, and to guide a biopsy needle to the target or region of interest for performance of a biopsy. In the illustrated embodiment, the imaging system 100 includes a support structure 101, a bottom detector unit 110, an upper detector unit 120, an imaging unit 130, an imaging unit positioning unit 150, an adaptor plate 160, a guide plate 170, a biopsy assembly 180, and a processing unit 190. It should be noted that the terms "upper" and "lower" are used for ease of clarity and illustration and, unless otherwise expressly stated, are not intended to limit the respective bottom and upper detector units to a particular orientation. For example, one or more aspects of the imaging system could be rotated 90 degrees such that the "bottom" and "upper" detector units were oriented as "left" and "right" detector units. Generally, in various embodiments, the upper and bottom detector units are generally directly opposite and facing each other to image an object therebetween in a particular plane. The bottom detector unit 110, the upper detector unit 120, and the imaging unit 130 may each contain one or more detectors configured for nuclear medicine (NM) imaging, such as single photon emission computed tomography (SPECT). The detector units, for example, may be configured as Cadmium Zinc Telluride (CZT) detectors.

Generally, an object to be imaged (e.g., a breast) may be positioned between the upper detector unit 120 and the bottom detector unit 110 to identify the location of a lesion in a given plane (e.g., an x-y plane as seen in FIG. 1). With the x-y position identified, the upper detector unit 120 may be retracted (e.g., moved upward and pivoted as seen in FIG. 1) from an upper detector imaging position to an upper detector clearance position. The upper detector unit 120 is shown in the upper detector clearance position in FIG. 1. With the upper detector unit 120 in the upper detector clearance position, the imaging unit 130 may be positioned above (or otherwise opposite) the bottom detector unit 120 with the object being imaged still in place. The imaging unit 130 may be utilized to determine a depth of the identified lesion (e.g., a position in a plane that is orthogonal or normal to the x-y plane of FIG. 1, such as the z plane). For example, an image or images obtained using the imaging unit 130 and the bottom detector unit 120 may be displayed with the depth determined manually be a user and/or automatically by the processing unit 190. With imaging unit 130 still in place, a biopsy may then be performed on the lesion using the biopsy assembly 180.

Generally, the processing unit 190 obtains or acquires imaging information from the bottom detector unit 110, the upper detector unit 120, and/or the imaging unit 130, and reconstructs an image using the imaging information to help locate a lesion to be biopsied with the biopsy assembly 180. The depicted processing unit 190 is operably coupled to the bottom detector unit 110, the upper detector unit 120, and the imaging unit 130. The processing unit 190, for example, may receive imaging information from the various detector or imaging units, reconstruct one or more images, and display the reconstructed images to a user. The user may provide an input to the processing unit 190, for example, identifying a lesion or region of interest in an image. As one example, based on the input, the processing unit 190 may determine a location of the lesion in an x-y plane, and the user may position the imaging unit 130 to align the imaging unit 130 (e.g., an opening or portion of an opening of the imaging unit 130) with the identified lesion. As another example, based on the input, the processing unit 190 may identify a depth of the lesion and provide an output to a user describing the depth. The user may then use the identified depth to set a depth of a biopsy needle or other biopsy tool. The processing unit 190 may provide control signals to one or more aspects of the imaging system 100, for example to position an imaging or detector unit. The processing unit 190 may include processing circuitry configured to perform one or more tasks, functions, or steps discussed herein.

The depicted processing unit 190 includes a reconstruction module 192, a display module 194, an input module 196, and a memory 198. It may be noted that other types, numbers, or combinations of modules may be employed in alternate embodiments, and/or various aspects of modules described herein may be utilized in connection with different modules additionally or alternatively. Generally, the reconstruction module 192 is configured to obtain imaging information from the upper detector unit 110, the bottom detector unit 120, and/or the imaging unit 130, and to reconstruct an image or images using the imaging information. The display module 194, for example, may include one or more display screens, and is configured to display the reconstructed images to a user. The user, for example, may identify a lesion on one or more images displayed using the display module 194. The display module 194 may also display instructions or prompts (e.g., instructions determined by the processing unit 190 responsive to user input) to a user. The input module 196 may include one or more of a keypad, mouse, touchscreen, or the like, and is configured to receive user input. For example, a reconstructed image may be displayed by the display module 194. A user may then identify one or more lesions on one or more displayed images. Responsive to the input, the processing unit 190 may determine a location of the lesion (e.g., a location in x-y plane and/or a depth) and display the determined location to the user. The user may then use the displayed information to perform subsequent imaging or biopsy activities. For example, a location in the x-y plane may be used by the user to position the imaging unit 130. As another example, a determined depth may be used by a user to set a depth of a biopsy needle or tool.

The support structure 101 supports the various components of the imaging system 100, positions the various components in a desired position or positions, and/or maintains the various components in a desired position. The depicted support structure 101 includes a support member 102, a detector body 104, and an upper detector positioning unit 106. The depicted support member 102 is oriented in a generally vertical direction, and may be a gantry in various embodiments. The detector body 104 is configured to support the various detector units or imaging units, and is also configured to be movable vertically (e.g., up and down as seen in FIG. 1) along the support member 102. In some embodiments, the detector body 104 may also be rotatable with respect to the support member 102. The depicted upper detector positioning unit 106 is mounted to the detector body 104, and is configured for moving the upper detector unit 120 between various positions (e.g., from an imaging position to a clearance position and/or vice versa). The upper detector positioning unit 106 may be configured to provide motion in a vertical direction, as well as to provide angling or tilting. For example, in the imaging position, a detector surface of the upper detector unit 120 may be generally parallel to a corresponding detector surface of the bottom detector unit 110, but the detector surface of the upper detector unit 120 may not be parallel to the corresponding detector surface of the bottom detector unit 110 when the upper detector unit 120 is in the clearance position. The upper detector positioning unit 106 may be configured for automatic or machine assisted motion of the upper detector unit 120 (e.g., using a motor or cylinder, among others), and/or may be configured for manual adjustment of the upper detector unit 120. For example, the upper detector positioning unit 106 may include guides to guide the upper detector unit 120 between positions, and/or securement mechanisms to lock or secure the upper detector unit 120 in place at a desired position.

The bottom detector unit 110 is mounted to the support structure 101. For example, the bottom detector unit 110 may fixedly mounted with respect to the detector body 104 and move with detector body 104 for positioning of the bottom detector unit 110 to image an object. The bottom detector unit 110 may be configured as a NM imaging detector and provide NM imaging information to the processing unit 190.

The upper detector unit 120 is mounted to the support structure 101 and is movable between an upper detector position (e.g., generally parallel to and facing the bottom detector unit 120 with an object positioned therebetween) and an upper detector clearance position (e.g., as seen in FIG. 1). With the upper detector unit 120 in the upper detector clearance position, the imaging unit 130 may be mounted to the support structure 101 (either directly or indirectly) and used for imaging the object, for example in conjunction with the bottom detector unit 110. The upper detector unit 120 in the depicted embodiment may be moved vertically respect to the bottom detector unit 110 (e.g., via the upper detector positioning unit 106), and may also be pivotable to be angled upward to provide additional clearance from the bottom detector unit 110 and/or to provide access to the adaptor plate 160. The upper detector unit 120 may be initially placed in the upper detector imaging position to obtain a planar image (e.g., in the x-y plane) in conjunction with the bottom detector unit 110, and then moved up and angled to provide clearance for positioning of the imaging unit 130. The upper detector unit 120 may be configured as a NM imaging detector and provide NM imaging information to the processing unit 190.

The imaging unit 130 is configured to be positionable in an imaging position (e.g., for determining a depth of a lesion in an object and performing a biopsy of the lesion with the imaging unit 130 still in the imaging position). The imaging unit 130 may also be removed from the imaging position. For example, the imaging unit 130 may pivot and/or linearly translate from the imaging position to allow use of the upper detector unit 120. As another example, the imaging unit 130 may be detached from a mounted imaging position and removed from the support structure 101 (e.g., removably detached from a member directly or indirectly mounted to the support structure 101). In various embodiments, the imaging unit 130 may be a molecular breast imaging (MBI) unit configured for imaging a breast. Generally, the imaging unit 130 includes an open area configured for access for biopsy tools while imaging is ongoing, or while the imaging unit 130 remains in the imaging position. The imaging unit 130 thus provides an example of open imaging unit, as the imaging unit includes an opening configured for access for a biopsy. In various embodiments, the imaging unit 130 provides for reliable and accurate determination of a lesion location as well as reliable and accurate positioning and use of biopsy tools.

Figure 2:
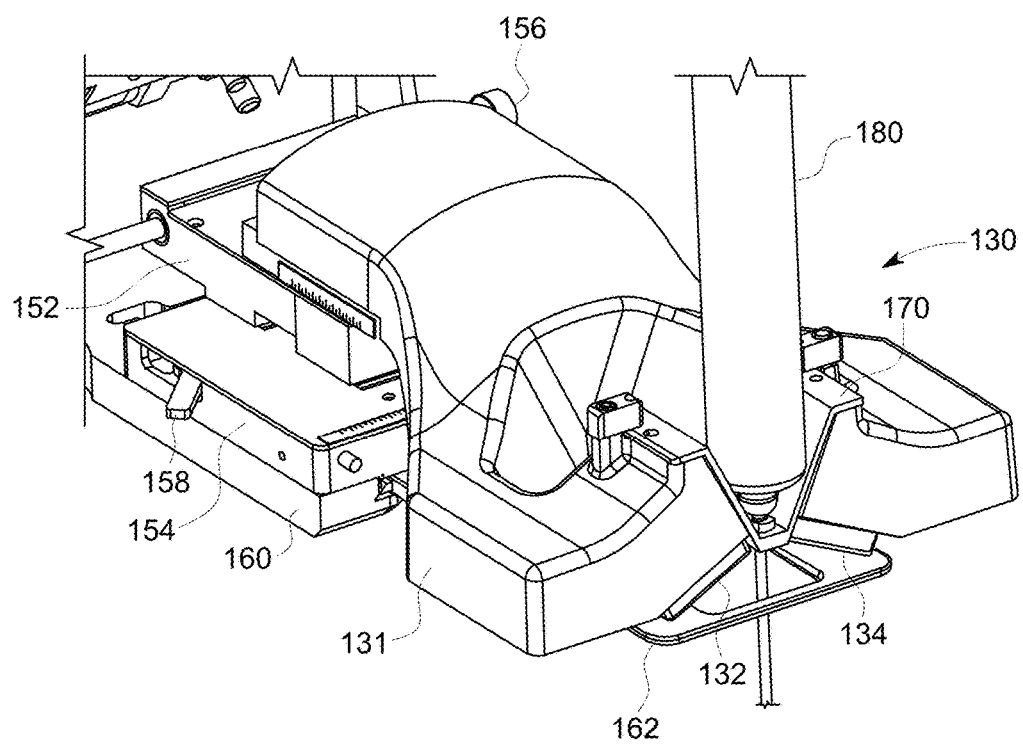
FIG. 2 is a perspective view schematic diagram of aspects of the imaging system of FIG. 1.
Figure 3:
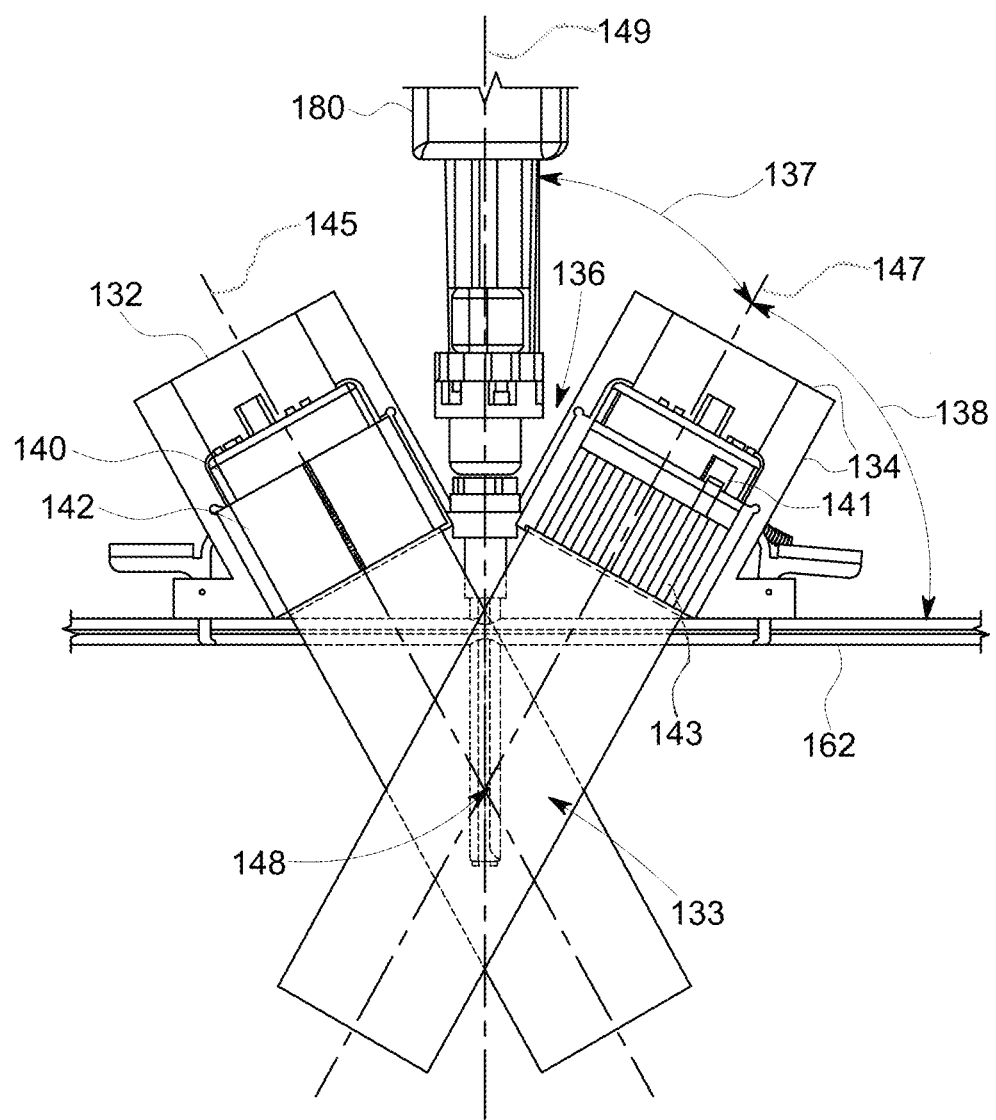
FIG. 3 is an end view schematic diagram of aspects of the imaging system of FIGS. 1 and 2.

A perspective view of the imaging unit 130 is shown in FIG. 2, and a schematic end view of the imaging unit 130 is shown in FIG. 3. The depicted imaging unit 130 includes a housing 131, a first detector unit 132, a second detector unit 134, and an opening 136. The depicted housing 131 is configured to protect and house the first detector unit 132 and the second detector unit 134, and to maintain the first detector unit 132 and the second detector unit 134 in a predetermined spatial relationship (e.g., at a predetermined distance and/or with a predetermined angle therebetween). The housing 131 is also configured to secure the imaging unit 130 to one or more aspects of the imaging system 100. For example, the housing 131 may include one or more tabs, notches, fasteners, latches, or the like to secure the housing 131 (e.g., a bottom surface of the housing 131) to the adaptor plate 160 (e.g., an upper surface of the adaptor plate 160). The housing 131 may be understood as being in an imaging position when the imaging unit 130 is in the imaging position.

The opening 136 is disposed between the first detector unit 132 and the second detector unit 134, and is configured to allow access to the object being imaged (e.g., breast) with the housing 131 (and imaging unit 131) in the imaging position. For example, the opening may be sized to allow access for biopsy tools and positioned so that a predetermined portion of the opening is aligned over a lesion to be biopsied (e.g., based on an x-y location of the lesion determined using an image generated using information from the upper detector unit 120 and the bottom detector unit 110). In the illustrated embodiment, the opening 136 extends between the first detector unit 132 and the second detector unit 134, and a has a generally rectangular shape when viewed from above. The sides of the opening 136 in the depicted embodiment are sloped such that the opening 136 is wider at a top portion (e.g., farther away from the object being imaged) and narrower at a bottom portion (e.g., closer to the object being imaged). For example, the wider access at the top may allow for easier use of a practitioner's fingers to manipulate a tool (e.g., biopsy needle), while the narrower access may provide access for a biopsy tool such as a needle. The opening 136 in the illustrated embodiment is also configured to accept the guide plate 170. For example, the guide plate 170 may be releasably securable to the opening 136.

The first detector unit 132 includes a first NM imaging detector 140 secured in the housing 131. The first detector unit 132 is configured to acquire first imaging information of an object (e.g., breast) being imaged when the imaging unit 130 (e.g., housing 131) is in the imaging position. As best seen in FIG. 3, the first detector unit 132 may be aligned along a first line of view 145 with the first imaging information thus acquired along the first line of view 145. The first NM imaging detector 140, for example, may be a CZT detector. As best seen in FIG. 3, the first detector unit 132 includes a first collimator 142 associated with the first NM imaging detector 140 and configured to control the direction of radiation that impacts upon the first NM imaging detector 140.

The second detector unit 134 may be similar in certain general respects to the first detector unit 132. For example, the second detector unit 134 includes a second NM imaging detector 141 secured in the housing 131. The second detector unit 134 is configured to acquire second imaging information of an object (e.g., breast) being imaged when the imaging unit 130 (e.g., housing 131) is in the imaging position. As best seen in FIG. 3, the second detector unit 134 may be aligned along a second line of view 147 with the second imaging information thus acquired along the second line of view 147. The second NM imaging detector 141, for example, may be a CZT detector. As best seen in FIG. 3, the second detector unit 134 includes a second collimator 143 associated with the second NM imaging detector 141 and configured to control the direction of radiation that impacts upon the second NM imaging detector 141.

With continued reference to FIG. 3, the first detector unit 132 and the second detector unit 134 are disposed symmetrically about a central axis 149 that passes through the opening 136. The biopsy assembly 180 may be directed along the central axis 149 when introduced between the first detector unit 132 and the second detector unit 134 (e.g., a hole of the guide plate 170 that receives a portion of the biopsy assembly 180 may be aligned with the central axis 149). The first line of view 145 and the second line of view 147 intersect the central axis 149, for example at a common point 148 as seen in FIG. 3. Based on an x-y position determined, for example using imaging information from the bottom detector unit 110 and the upper detector unit 120, the imaging unit 130 may be positioned so that the central axis 149 is aligned with and passes through the identified lesion.

In the illustrated embodiment, for example, the second line of view 147 may be disposed at an angle 138 from the horizontal (e.g., from a surface parallel to a surface of the bottom detector unit 110 or from a line passing along a plane defined by the x-y directions. Further, the second line of view 147 may be disposed at an angle 137 from the vertical (e.g., from the central axis 149). The angle 138 may be about 60 degrees and the angle 137 may be about 30 degrees, such that the first line of view 145 and the second line of view 147 may be disposed at an angle of about 60 degrees with respect to each other, or such that the first line of view 145 and the second line of view 147 define an angle therebetween of about 60 degrees. The depicted arrangement is provided by way of example, as other arrangements may be utilized in alternate embodiments. Generally, the first detection unit 132 and the second detection unit 134 may be configured to have at least partially overlapping fields of view defining a common field of view 133. If the lesion is located within the common field of view 133, for example, the depth of the lesion may be determined using the first imaging information from the first detection unit 132 and the second imaging information from the second detection unit 134.

As best seen in FIG. 2, the depicted imaging unit positioning unit 150 is configured to provide for adjustability of the imaging unit 130, for example with respect to the x-y plane (e.g., a plane generally parallel to a plane defined by a detecting surface of the bottom detector unit 110). In the illustrated embodiment, the imaging unit positioning unit 150 includes an upper portion 152, a lower portion 154, a motion assembly 156, and a securement assembly 158. The upper portion 152 is configured to be secured to the housing 131 (e.g., to a bottom surface of the housing 131). The lower portion 154 of the imaging unit positioning unit 150 is configured to be mounted to the support structure 101, for example via mounting to the adaptor plate 160 which is in turn mounted directly or indirectly to the support structure 101. The upper portion 152 and the lower portion 154 are movable with respect to each other, such that the housing 131 may be movable with respect to the adaptor plate 160. Thus, the housing 131 may be positioned as desired, for example to align the opening 136 or a portion thereof (e.g., the central axis 149) with a determined location of a lesion (e.g., a location determined in the x-y plane). The motion assembly 156 may be utilized to position the housing 131 as desired. In the illustrated embodiment, the motion assembly 156 includes a shaft actuated by a wheel or knob. As the shaft rotates, the upper portion 152 is articulated along the lower portion 154 in the axial direction of the shaft. Only one shaft is shown in FIG. 2 for ease of illustration; however, more than one shaft may be employed (e.g., one shaft for motion in the x direction and one shaft for motion in the y direction). The motion assembly 156 may be articulated by a user turning the wheel or, in some embodiments, may be automatically or autonomously controlled by the processing unit 190 to position the imaging unit 131 as desired. In various embodiments, the processing unit 190 may determine a setting or position for the motion assembly 156, and instructions regarding the determined setting or position may be displayed via the display module 194. The securement assembly 158 may include one or more latches, tabs, or the like, and is used to secure the bottom portion 154 of the imaging unit positioning unit 150 to the adaptor plate 160 (e.g., to an upper surface of the adaptor plate 160).

Figure 4:
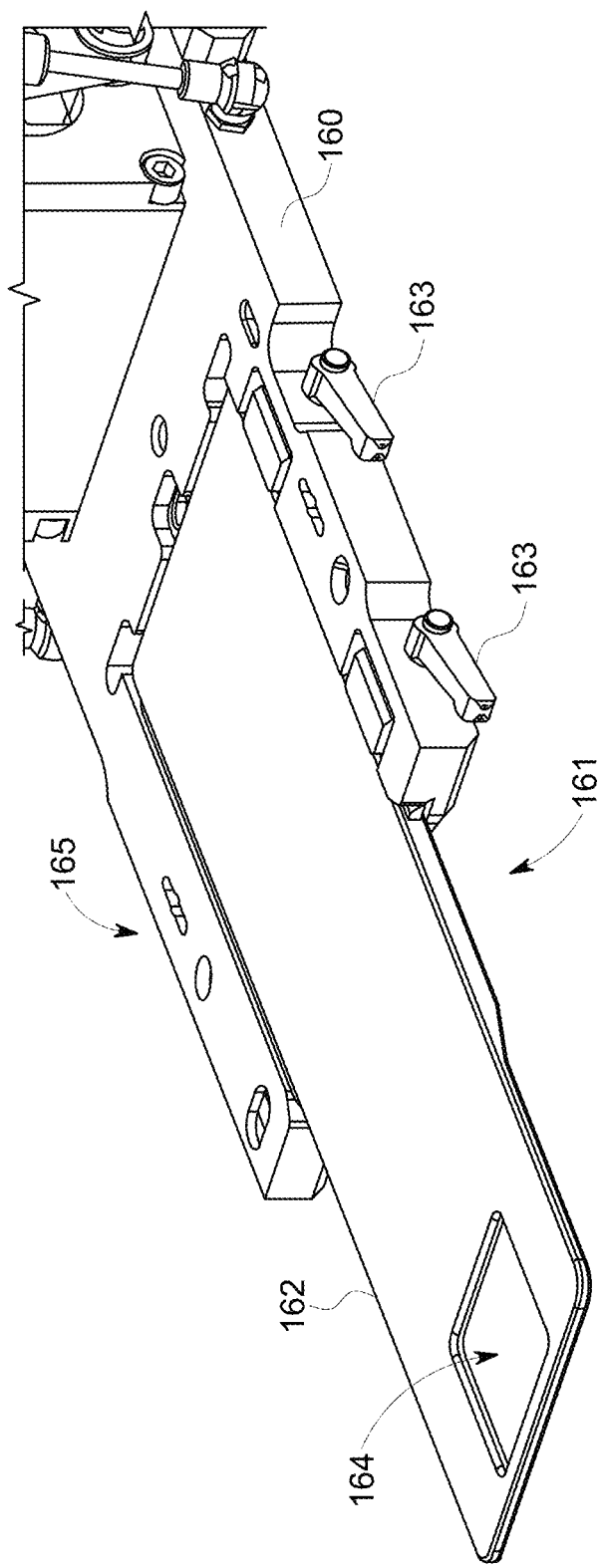
FIG. 4 provides a perspective view of an adaptor plate of the imaging system of FIG. 1 in accordance with various embodiments.

FIG. 4 provides a perspective view of the adaptor plate 160 and the compression paddle 162 in accordance with various embodiments. Generally, the adaptor plate 160 may be secured to the support structure 101 (e.g., to the detector body 104), and is configured for mounting the imaging unit 130. In the illustrated embodiment, the adaptor plate 160 is oriented substantially parallel to the bottom detector unit 110 (e.g., substantially parallel to a detector surface of the bottom detector unit 110). In the illustrated embodiment, the adaptor plate 160 is configured to accept the lower portion 154 of the imaging unit positioning unit 150, with the imaging unit positioning unit 150 in turn mounted to the imaging unit 130. Further, the adaptor plate 160 may be configured to secure the upper detector unit 120 in place, for example, when the upper detector unit 120 is used for imaging. In the illustrated embodiment, the adaptor plate 160 includes one or more openings 165 configured to accept features of the imaging unit positioning unit 150 and/or the upper detector unit 120. The openings 165 may be configured as one or more of slots or round holes, among others. The depicted adaptor plate 160 also includes a paddle opening 161 configured to accept at least a portion of the compression paddle 162 for mounting thereto.

As seen in FIG. 4, the compression paddle 162 is configured to be mounted to the adaptor plate 160. The compression paddle 162 is configured to compress the object (e.g., breast) being imaged, for example when the imaging unit 130 is used to determine or confirm a depth of a lesion within the object. The compression paddle may be made of a biocompatible material. The adaptor plate 160 may include securement members 163 configured to secure the compression paddle 162 in place. For example, the securement members 163 may include a cam used to actuate gripping portions toward (to secure) and away (to release) from sides of the compression paddle 162. As also seen in FIG. 4, the compression paddle 162 includes an opening 164. The opening 164 is configured to provide access during a biopsy procedure. For example, the opening 164 of the compression paddle 162 may be aligned with the opening 136 of the imaging unit 131 when the compression paddle 162 and imaging unit 131 are secured to the adaptor plate 160. In some embodiments, the opening 164 may have a generally square cross-section of about 5.5 centimeters by about 5.5 centimeters, and be positioned near an edge of the compression paddle 162. The edge of the opening 164 may be configured to be aligned with an edge of a field of view (FOV) of one or more detectors of the imaging unit 130, for example to provide access to lesions positioned close to a chest wall. The compression paddle 164 may have a thickness that is relatively small to minimize or reduce attenuation of imaging information by the compression paddle 164, while providing sufficient strength or rigidity to help immobilize the object being imaged and/or biopsied.

Figure 5:
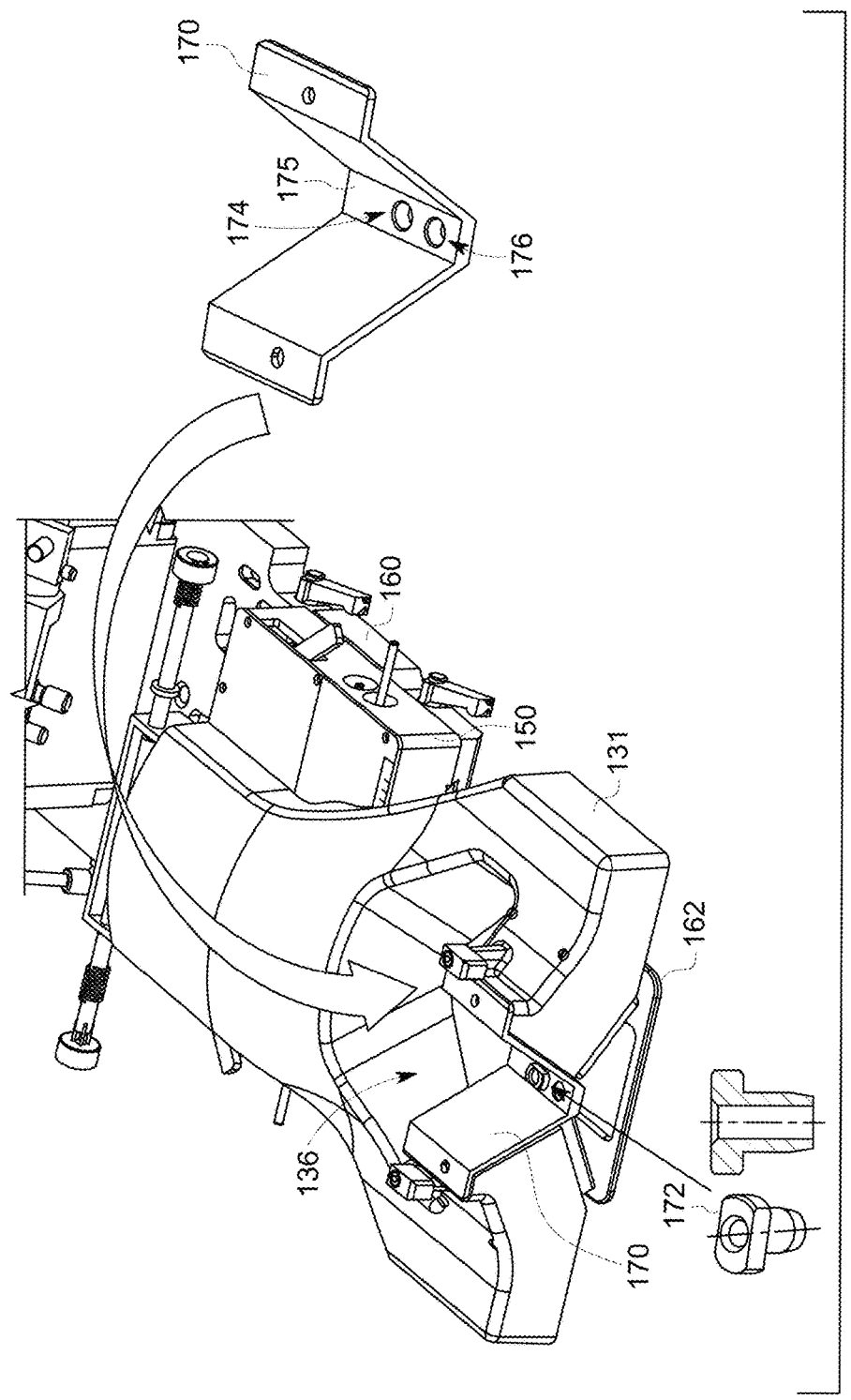
FIG. 5 provides a perspective view of the imaging system of FIG. 1 including a guide plate in accordance with various embodiments.

FIG. 5 provides a perspective view of the imaging unit 130 and related components including the guide plate 170. The depicted guide plate 170 is generally "V" shaped and is configured to be secured in the opening 136 between the first detector unit 132 and the second detector unit 134. The guide plate 170 is configured to be removably mounted to the opening 136, for example using one or more of fasteners, latches, tabs, or the like. The depicted guide plate 170 is configured to accept at least a portion of the biopsy assembly 180 (e.g., an insertion member of the biopsy assembly 180), and to direct the at least a portion of the biopsy assembly 180 along the central axis 149 of the opening 136 or other portion of the opening aligned with the lesion to be biopsied.

As seen in FIG. 5, the guide plate 170 includes a first hole 174 and a second hole 176, each of which penetrate a bottom surface 175 of the guide plate 170. The first hole 174, for example, may be utilized to guide the biopsy assembly 180 for procedures involving lesions that are not proximate the chest wall. The second hole 176 may be used for procedures involving lesions that are proximate he chest wall. In the illustrated embodiment, the guide plate 170 and housing 131 are sized and configured so that the first hole 174 is aligned with the central axis 149 when the guide plate 170 is mounted to the opening 136 of the housing 131 and positioned in the imaging position (e.g., with the housing 131 positioned based on a determined lesion location in the x-y plane). (It may be noted that, for example for a lesion located close to a chest wall, the housing 131 may be positioned so that the second hole 176 is aligned with the lesion). In the illustrated embodiment, a bushing 172 is configured to be placed in the first hole 174 and/or the second hole 176, and is configured to provide a snug fit for an insertion portion of the biopsy assembly 180. It may be noted that alternative or additional guide plates may be used in some embodiments. For example, a guide plate having a slot extending along a portion of the length of the surface 175 (e.g., such that a majority of the surface area of the surface 175 is removed) may be used for cleaning a surface of the object being imaged and/or biopsied, to anesthetize the surface, and/or to make an incision in the surface. The guide plate 170 may be sterilized in various embodiments.

Figure 6:
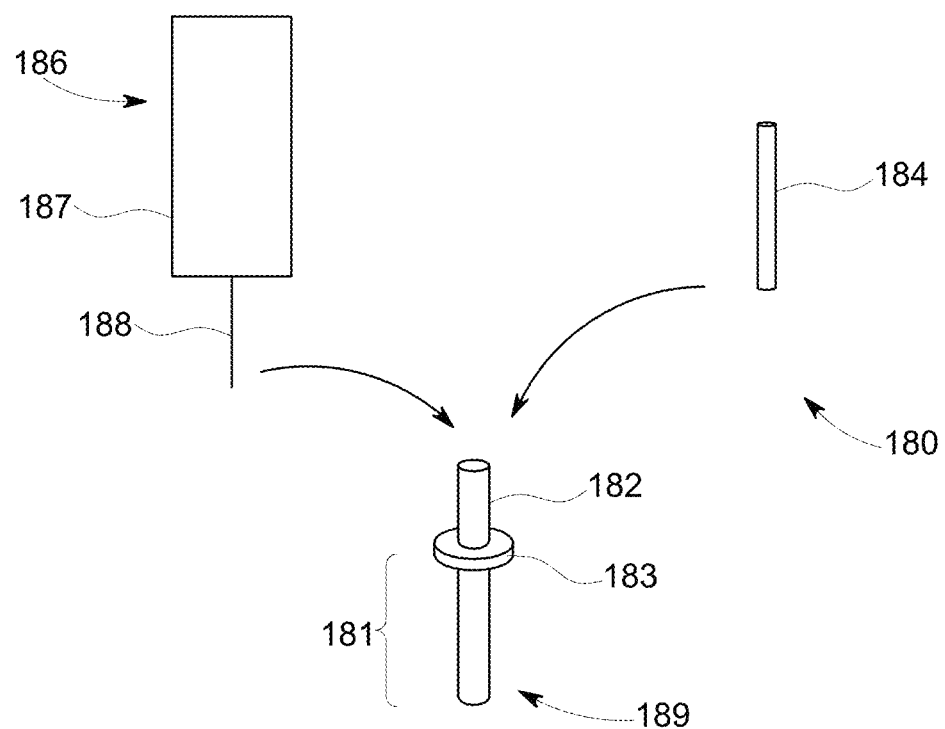
FIG. 6 illustrates a biopsy assembly in accordance with various embodiments.

FIG. 6 illustrates the biopsy assembly 180. The depicted biopsy assembly 180 includes an insertion member 182, a depth confirmation member 184, and a biopsy collection unit 186. Generally, the insertion member 182 is configured to be inserted through the guide plate 170 (e.g., through the bushing 172) with a distal end 189 of the insertion member 182 proximate a lesion identified (e.g., a lesion having a depth determined using the imaging unit 130) with the imaging system 100. The insertion member 182 may have a puncturing feature or device at or near a distal end 189 of the insertion member 182 configured to puncture a lesion. The depth confirmation member 184 may be inserted into the insertion member 182. The depth confirmation member 184 is configured to be visible on an image reconstructed using the imaging information from the imaging unit 130 (e.g., the depth confirmation member 184 may be radioactive), and is used to provide a visual confirmation of the depth of the lesion. For example, if the depth confirmation member 184 is positioned at the determined depth, yet is not in contact with or proximate to the lesion as seen in an image reconstructed using imaging information collected via the imaging unit 130 while the depth confirmation member 184 was positioned at the determined depth, then the determined depth (and/or determined x-y location) may be adjusted accordingly. The biopsy collection unit 186 includes a needle 188 and a reservoir 187. The needle 188 is configured to penetrate a lesion, with the reservoir 187 configured to collect material drawn from the lesion. The reservoir 187 may have a plunger or other device configured to apply a vacuum to draw material out of the lesion after the needle 188 is inserted into the lesion.

The insertion member 182 may be a generally tube-shaped member having an outer diameter configured for insertion into the bushing 172 and an inner diameter configured to accept the needle 188 and the depth confirmation member 184. In the illustrated embodiment, the insertion member includes an adjustable stop 183 configured to be positioned along a length of the insertion member 182 at a location providing an insertion distance 181 corresponding to the depth of a lesion to be biopsied. The adjustable stop 182 may have an outside diameter greater than the inside diameter of the bushing 172, such that the stop is prevented from being inserted beyond an upper surface of the bushing 172 and the distal end 189 of the insertion member is prevented from advancing more than the insertion distance 181 past the upper surface of the bushing 172. It may be noted that the insertion distance may be different than the depth. For example, the insertion distance 181 may be set as the depth plus an offset distance from a surface of the object having the lesion within to an upper surface of the bushing 172. It may be noted that, in various embodiments, the depth confirmation member 184 and/or the needle 187 may include adjustable stops configured to prevent insertion past a desired depth corresponding to an identified lesion location. In various embodiments, the processing unit 190 may determine the insertion distance 181 (e.g., based on the determined depth as well as an offset distance between a bushing (or other) surface and an object surface), and instructions regarding the determined insertion distance 181 may be displayed via the display module 194.

Figure 7:
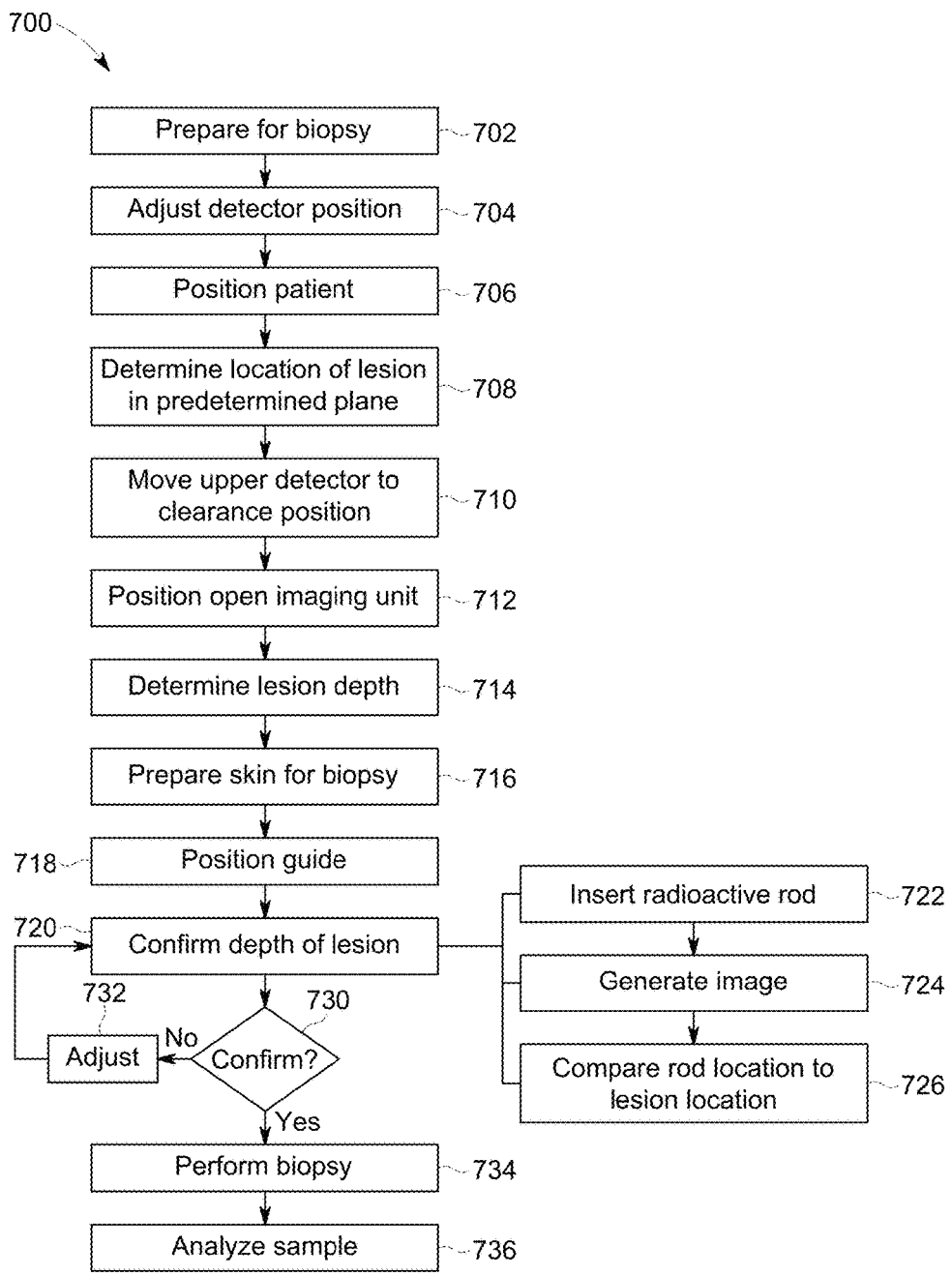
FIG. 7 is a flowchart of a method in accordance with various embodiments.

FIG. 7 provides a flowchart of a method 700 for performing a biopsy (e.g., including identifying a location of a lesion to be biopsied). The method 700, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 700 may be able to be used as one or more algorithms to direct hardware (e.g., one or more aspects of the processing unit 190) to perform one or more operations described herein.

At 702, a biopsy is prepared for. For example, various components may be prepared for use. In some embodiments, an imaging unit for use during a biopsy (e.g., imaging unit 130) may be stored separately from a support structure (e.g., support structure 101) or stored in a compartment of the support structure. The imaging unit may be removed from a storage location and electrically coupled (e.g., coupled to a processing unit such as the processing unit 190) to an imaging system. Additionally or alternatively, a compression paddle (e.g., compression paddle 162) may be mounted to the support structure (e.g., mounted to an adaptor plate such as adaptor plate 160). To mount the compression paddle, an upper detector (e.g., upper detector 120 may be cleared or positioned a distance from the adaptor plate. Once positioned, the compression paddle 162 may be secured in place, for example via locking handles actuated to secure the compression paddle to the adaptor plate.

At 704, a detector position is adjusted. For example, upper and lower detector units (e.g., upper detector unit 120 and bottom detector unit 110) may be positioned generally horizontally opposed to each other in a predetermined orientation (e.g., vertical for a vertical approach or horizontal for a lateral approach). The upper detector may be secured to the adaptor plate as part of adjusting the detector position. The detectors may generally be positioned to accept an object to be imaged (e.g., a breast of a human patient).

At 706, a patient is positioned. For example, a breast of the patient may be positioned between the upper and bottom detectors. In some embodiments, the breast is placed on the bottom detector with a believed or potential lesion location placed generally centered beneath an opening of a compression paddle associated with the upper detector. The breast and/or upper and bottom detectors may then be rotated to place the lesion as close as possible to the compression paddle. The upper detector may then be lowered (or otherwise advanced toward the bottom detector) until the breast is effectively immobilized by the compression paddle.

At 708, a scan is performed to identify a location of the lesion in a predetermined plane (e.g., in an x-y plane). The scan may be performed with the upper and bottom detectors generally parallel with the breast interposed therebetween, and with the compression paddle between the upper detector and the breast. Imaging information obtained or acquired via the scan may be used to determine the planar (e.g., x-y) location of the lesion.

Figure 8:
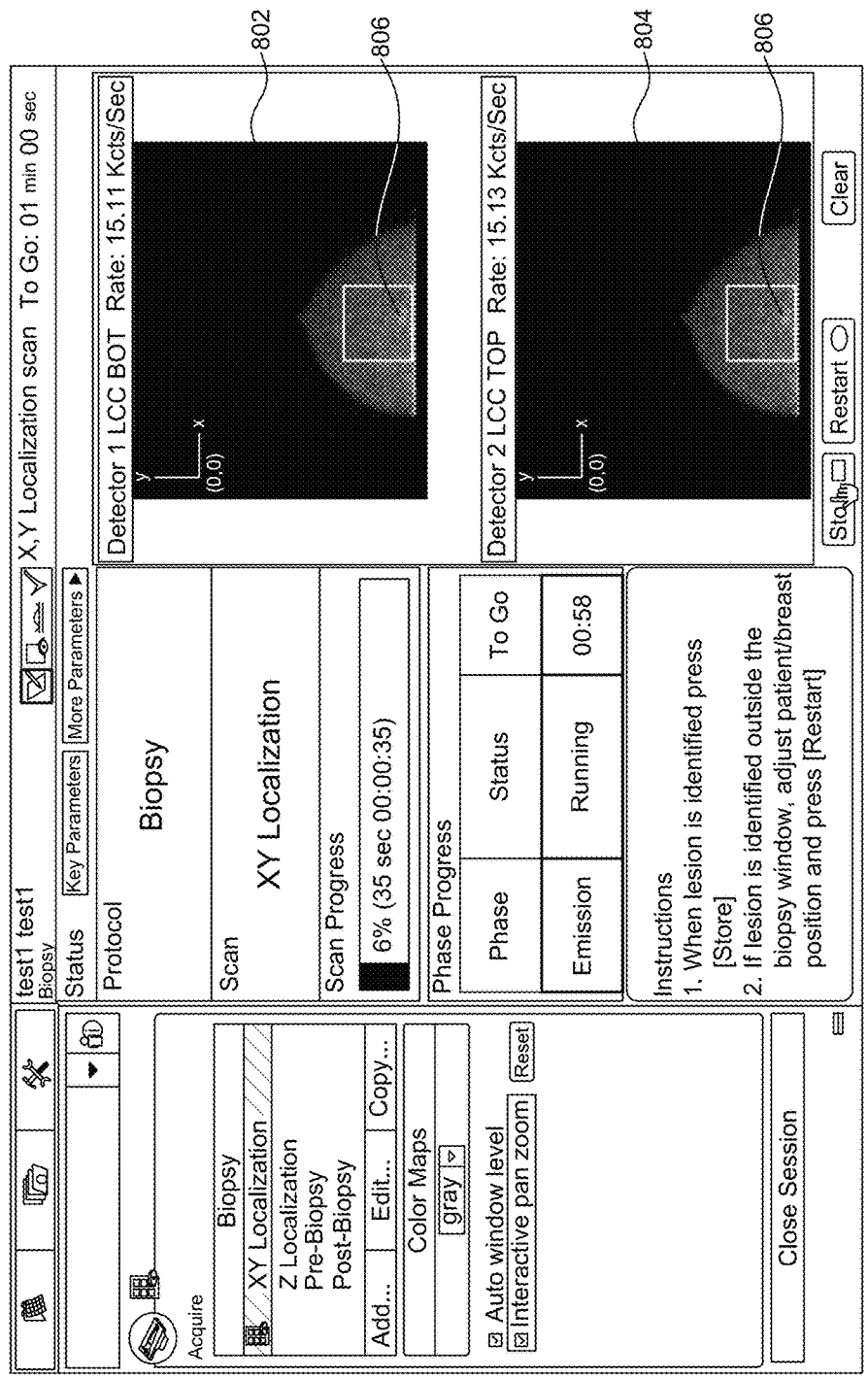
FIG. 8 illustrates example images from bottom and upper detectors used to identify a location in a plane of a lesion in accordance with various embodiments.

For example, FIG. 8 illustrates an example display (e.g., a display provided via display module 194) of images reconstructed using information obtained by the scan at 708. For example, a first view 802 may be provided using information from the bottom detector, and a second view 804 may be provided using information from the upper detector. A lesion 806 may be identified in each view, for example by a user positioning a cursor over the lesion 806 and selecting a location corresponding to the lesion 806. One or more processors (e.g., processing unit 190) may determine the x-y location of the lesion 806 based on the user input.

Returning to FIG. 7, at 710, the upper detector is moved to the clearance position. Once the x-y location of the lesion is determined, the upper detector may be moved from an imaging position to the clearance position. For example, one or more manual mechanisms may be used to release the upper detector from a located imaging position and to translate and/or tile the upper detector from the imaging position to the clearance position. Once in the clearance position, the upper detector may be locked or secured in place.

At 712, an open imaging unit (e.g., imaging unit 130 or other imaging unit configured to provide access for biopsy tools while the imaging unit is in an imaging position) is mounted and positioned. For example, the imaging unit 130 may be mounted via a positioning unit to the same adaptor plate to which the compression paddle is mounted. Notably, the breast may be maintained in position under compression from the compression paddle while the upper detector is cleared and the open imaging unit is positioned, thereby reducing or eliminating any motion of the lesion from the position identified or determined at 708. The open imaging unit may be positioned with a central portion (e.g., central axis) of an opening aligned with or otherwise corresponding to the determined x-y position. The open imaging unit may be positioned manually (e.g., to a location indicated by a display) and/or using machine feedback based on the determined x-y location of the lesion. For example, a specific setting of a knob or other mechanism of the positioning unit may be displayed by a display unit of the imaging system. With the imaging unit positioned, the lesion is positioned in a predetermined relationship with an opening of the imaging unit, with the opening of the imaging unit aligned with the lesion for convenient access through the opening, and/or with the lesion symmetrically and/or directly aligned with plural detector units of the imaging unit for reliable and accurate depth determination of the lesion.

At 714, a scan is performed to identify the lesion depth. For example, imaging information may be acquired from the bottom detector unit, as well as from first and second detectors of the open imaging unit. The first and second detector units may be angled with respect to each other, and have lines of views that intersect each other and a central axis or other axis corresponding to the lesion location. (See, e.g., FIG. 3 and related discussion herein.) With the lesion appearing in images from each of the first and second detector units, one or more processors (e.g., processing unit 190) may determine the depth of the lesion based on the angles of the lines of view of the first and second detectors as well as the position of the lesion within the corresponding images. The position of the lesion as shown on one or more images may be determined using manual input.

Figure 9:
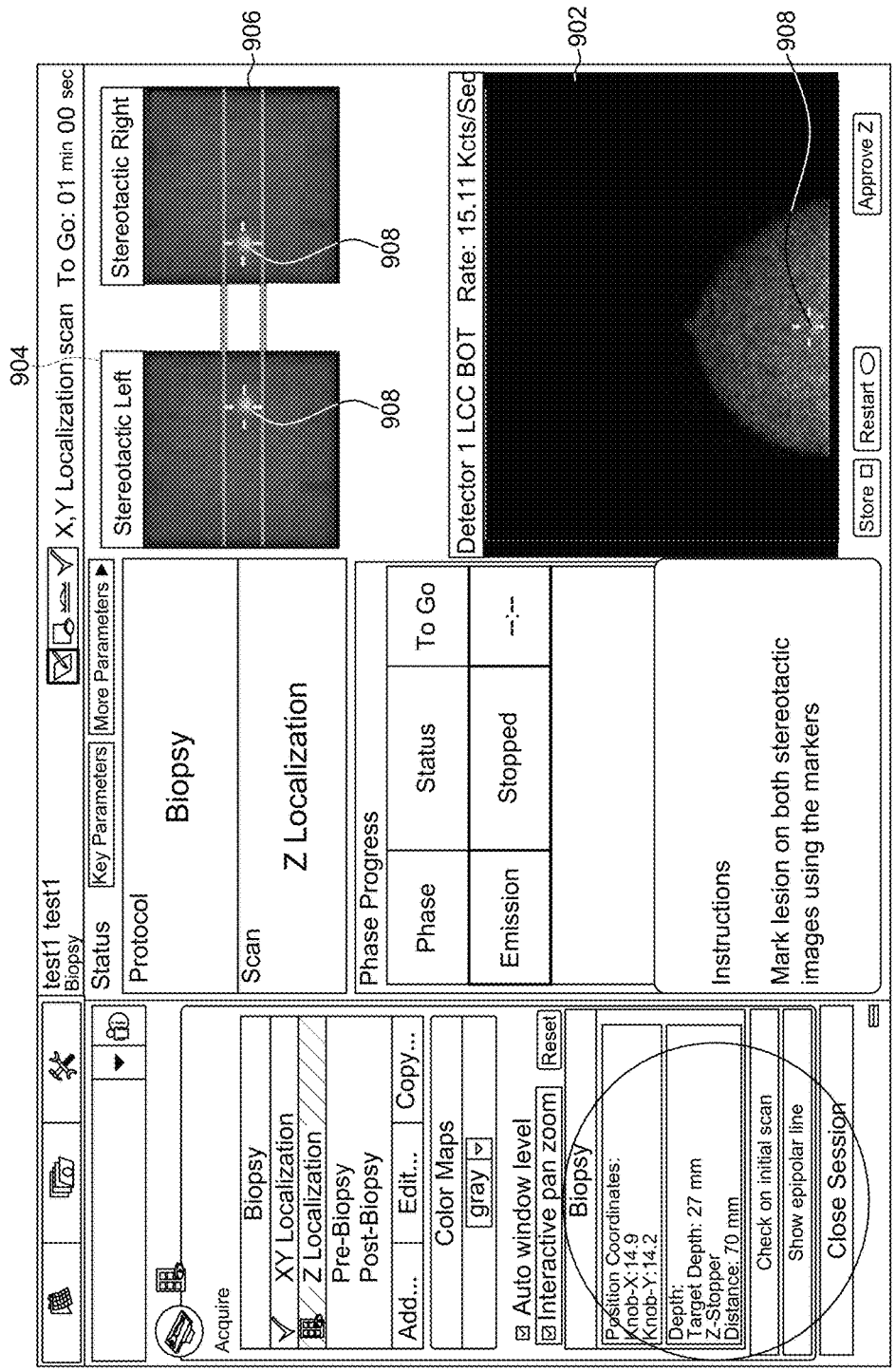
FIG. 9 illustrates example images from an open imaging unit used to identify a depth of a lesion in accordance with various embodiments.

For example, FIG. 9 illustrates an example display (e.g., a display provided via display module 194) of images reconstructed using information obtained by the scan at 714. For example, a bottom view 902 may be provided using information from the bottom detector, a left view 904 may be provided using information from a first detector of the open imaging unit, and right view 906 may be provided using information from a second detector of the open imaging unit. A lesion 908 may be identified in each view, for example by a user positioning a cursor over the lesion 908 and selecting a location corresponding to the lesion 908. One or more processors (e.g., processing unit 190) may determine the depth of the lesion 908 based on the user input.

At 716, with the depth (as well as x-y location) of the lesion determined, the skin is prepared for biopsy. The skin may be prepared for biopsy with the open imaging unit still in place in an imaging position. For example, a guide plate having a slot may be positioned in the opening of the open imaging unit. The slot may have a width of about 18 millimeters to provide access for a scalpel and/or anesthesia needle. The anesthesia needle may be used to anesthetize the object (e.g., breast), and an incision subsequently made (e.g., with a scalpel) to provide access for biopsy tools.

At 718, with the incision made, a needle guide (e.g., guide plate 170 and bushing 172) is positioned in the opening of the open imaging unit. A display of the imaging system may provide instructions for use of the guide plate (e.g., to utilize first guide hole 174 if lesion is not near chest wall, to utilize second guide hole 176 if lesion is near chest wall). An insertion member of a biopsy assembly may next be inserted through the needle guide. An adjustable stop may be positioned on the insertion member so that the insertion member extends into the breast to the depth of the lesion.

At 720, the depth of the lesion is confirmed (the x-y location may be confirmed as well). For example, the breast and lesion within the breast may have moved during one or more steps of the method 700, or the open imaging unit may have been mis-positioned. In the illustrated embodiment, the depth of the lesion is confirmed using various substeps. For example, at 722, a radioactive rod is inserted into the insertion member and advanced until the radioactive rod reaches the determined depth of the lesion within the breast. In some embodiments, only a distal end or distal portion of the radioactive rod may be radioactive. At 724, an image is generated using imaging information from the first and second detectors of the open imaging unit (and, optionally, the bottom detector unit) with the radioactive rod in place. The radioactive rod appears in the imaging information and may be used to confirm the depth. At 726, the location of a distal end of the radioactive rod is compared to the lesion location. For example, images of the breast with the radioactive rod inserted may be displayed to a practitioner or user. The practitioner or user may then make a visual determination of whether the distal end of the radioactive rod is at a desired position adjacent to or proximate the lesion.

Figure 10:
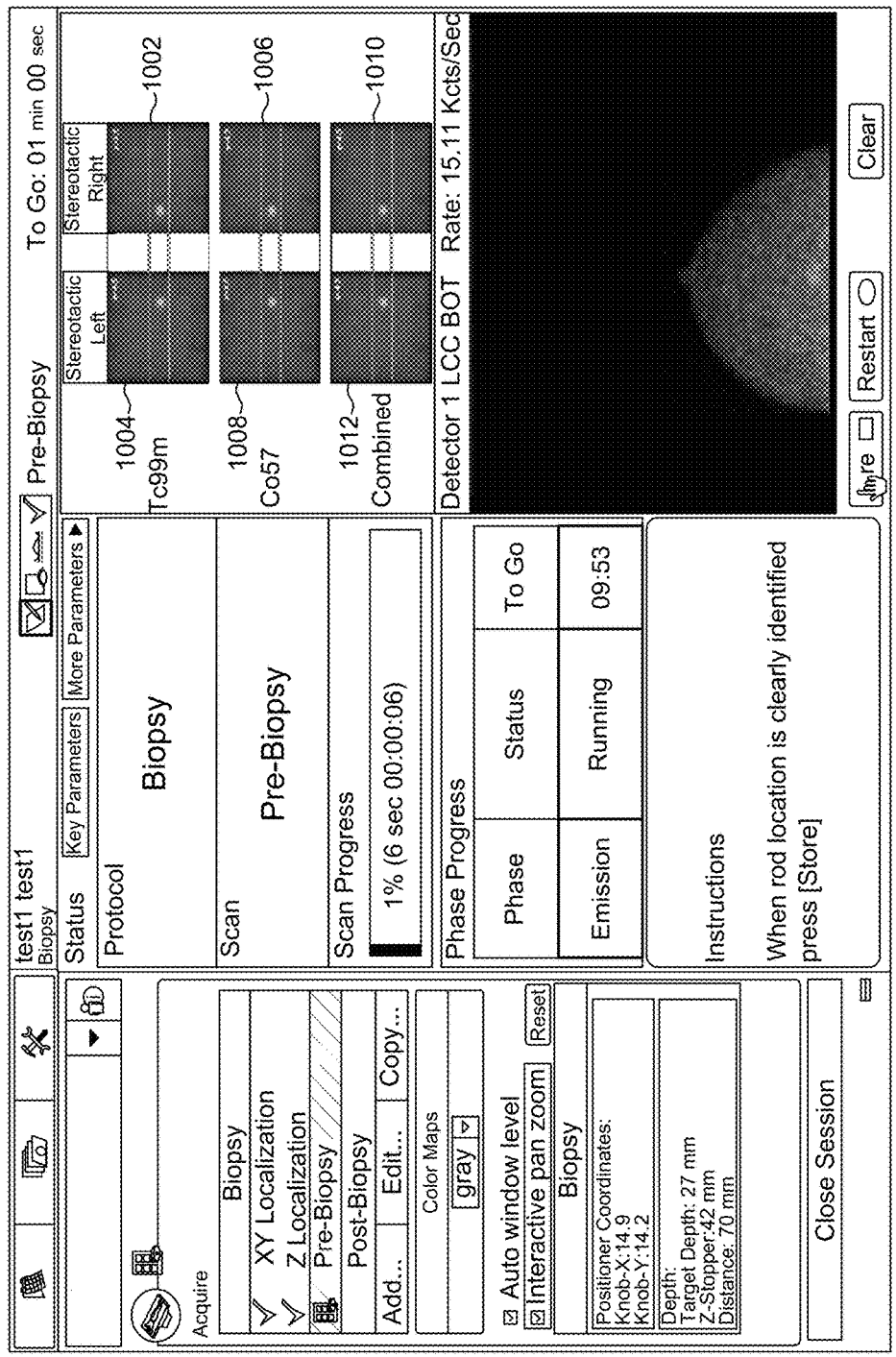
FIG. 10 illustrates example images used to confirm a location of a lesion in accordance with various embodiments.

For example, FIG. 10 illustrates various view of images (e.g., displayed via display module 194) reconstructed using information obtained by a bottom detector and open imaging unit with a radioactive rod inserted. Views 1002 and 1004 show right and left views using a radioactive tracer (e.g., Technetuim 99m (Tc99m)) indicating the position of the lesion. Views 1006 and 1008 show right and left views of an end of a radioactive rod (e.g., a rod comprising a radioactive material such as Cobalt 57 (Co57)). Views 1010 and 1012 show right and left views combining the lesion and end of the radioactive rod. If the end of the rod and the lesion location are substantially similar, the depth may be confirmed, but if the end of the rod and lesion location are not substantially similar, the depth may be identified as incorrect.

At 730, if the depth (or the x-y position or location of the open imaging unit with respect to the determined x-y location of the lesion) is not confirmed (e.g., the distal end of the biopsy insertion member is not positioned as desired as indicated by the position of the radioactive rod), the method 700 may proceed to 732, and the depth (and/or x-y positioning of the open imaging unit) adjusted. After the depth is adjusted, the method 700 may return to 720 for confirmation that the adjusted depth provides a desired position of the biopsy insertion member. If the depth is confirmed, the method may proceed to 734.

At 734, a biopsy is performed. For example, a biopsy needle may be inserted into the lesion via the biopsy insertion member and used to collect a sample from with the lesion. With the depth determined and/or confirmed using the open imaging unit, the location of the lesion may be accurately and reliably known, such that the biopsy needle is reliably and accurately positioned to collect material from the lesion, reducing or eliminating the need to perform multiple insertions, adjustments, and/or biopsies to collect material from the lesion instead of surrounding tissue. At 736, the sample or specimen may be analyzed.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A molecular breast imaging (MBI) unit comprising;
a housing configured to be positioned in an imaging position for imaging a single breast;
a first detector unit comprising a first nuclear medicine (NM) imaging detector secured in the housing, the first detector unit configured to acquire first imaging information of the single breast when the housing is in the imaging position; and
a second detector unit comprising a second NM imaging detector secured in the housing, the second detector unit configured to acquire second imaging information of the single breast when the housing is in the imaging position, wherein the first detector unit and the second detector unit are fixed in a predetermined spatial relationship with respect to each other and at a fixed, predetermined distance from each other, and configured to be disposed about the single breast;
wherein the housing comprises an opening disposed between the first detector unit and the second detector unit, the opening configured to allow access by a biopsy assembly to the single breast with the housing in the imaging position.

2. The molecular breast imaging (MBI) unit of claim 1, wherein the first detector unit defines a first line of view and the second detector unit defines a second line of view, the first line of view and second line of view each intersecting a central axis defined by the opening.

3. The molecular breast imaging (MBI) unit of claim 2, wherein the first line of view and the second line of view are not parallel to each other.

4. The molecular breast imaging (MBI) unit of claim 2, wherein the first line of view and the second line of view define an angle therebetween of about 60 degrees.

5. The molecular breast imaging (MBI) unit of claim 1, further comprising a guide configured to be removably mounted to the opening, the guide configured to accept an insertion member of the biopsy assembly and to direct the insertion member of the biopsy assembly along a central axis of the opening, wherein the guide comprises two or fewer openings configured to accept the insertion member.

6. The molecular breast imaging (MBI) unit of claim 1, wherein the first nuclear medicine (NM) imaging detector and the second NM imaging detector are Cadmium Zinc Telluride (CZT) detectors.

7. The molecular breast imaging (MBI) unit of claim 1, wherein the first and second detectors are the only detectors of the molecular breast imaging (MBI) unit.

8. An imaging system comprising:
a bottom detector unit mounted to a support structure;
an upper detector unit mounted to the support structure, the upper detector unit movable from an upper detector imaging position to an upper detector clearance position; and
an imaging unit configured to be mounted to the support structure in an imaging position when the upper detector unit is in the upper detector clearance position, the imaging unit comprising:
a housing;
a first detector unit comprising a first nuclear medicine (NM) imaging detector secured in the housing, the first detector unit configured to acquire first imaging information of an object when the imaging unit is in the imaging position; and
a second detector unit comprising a second NM imaging detector secured in the housing, the second detector unit configured to acquire second imaging information of the object when the housing is in the imaging position, wherein the first detector unit and the second detector unit are at a fixed, predetermined distance from each other;
wherein the housing comprises an opening disposed between the first detector unit and the second detector unit, the opening configured to allow access by a biopsy assembly to the object with the housing in the imaging position, wherein the first detector unit and the second detector unit are disposed on an opposite side of the object from the bottom detector unit when the imaging unit is in the imaging position.

9. The imaging system of claim 8, further comprising an adaptor plate secured to the support structure and configured for mounting the imaging unit, the adaptor plate oriented parallel to the bottom detector unit.

10. The imaging system of claim 9, further comprising a compression paddle configured to be mounted to the adaptor plate, the compression paddle configured to compress the object being imaged and including a compression paddle opening aligned with the opening of the imaging unit.

11. The imaging system of claim 9, further comprising an imaging unit positioning unit, the imaging unit positioning unit comprising an upper portion and a lower portion, the lower portion configured to be secured to the adaptor plate and the upper portion configured to be secured to the housing of the imaging unit, the upper portion and lower portion movable with respect to each other, wherein the housing of the imaging unit is movable with respect to the adaptor plate.

12. The imaging system of claim 8, further comprising a guide configured to be removably mounted to the opening, the guide configured to accept an insertion member of a biopsy assembly and to direct the insertion member of the biopsy assembly along a central axis of the opening, wherein the guide comprises two or fewer openings configured to accept the insertion member.

13. The imaging system of claim 12, further comprising a radioactive member, the radioactive member configured to be accepted by the insertion member of the biopsy assembly, wherein the radioactive member is detected by the first detector unit and the second detector unit when inserted into the insertion member of the biopsy assembly.

14. The imaging system of claim 8, wherein the first detector unit defines a first line of view and the second detector unit defines a second line of view, the first line of view and second line of view each intersecting a central axis defined by the opening.

15. The imaging system of claim 8, wherein the first line of view and the second line of view are not parallel to each other.

16. A method comprising:
- determining, with one or more detector units, a location of a region of interest within a single breast with respect to a first dimension and a second dimension;
- positioning an imaging unit in an imaging position proximate the single breast, wherein the imaging unit comprises a housing, a first detector unit, and a second detector unit, wherein the housing comprises an opening disposed between the first and second detector units, the opening configured to allow access by a biopsy assembly to the single breast when the imaging unit is in the imaging position, wherein a central axis of the opening is aligned with the region of interest when the imaging unit is in the imaging position wherein the first detector unit and the second detector unit are fixed in a predetermined spatial relationship with respect to each other and at a fixed, predetermined distance from each other, and disposed about the single breast; and
- determining, using imaging information from the first detector unit and the second detector unit, a depth of the region of interest from a surface of the single breast, the depth extending from a plane defined by the first dimension and the second dimension.

17. The method of claim 16, further comprising inserting a biopsy needle through the opening of the housing into the single breast at the depth determined using the imaging information from the first detector unit and the second detector unit, and performing a biopsy of the region of interest.

18. The method of claim 17, wherein region of interest is a lesion within the single breast.

19. The method of claim 17, wherein the biopsy is performed with the imaging unit in the imaging position.

20. The method of claim 17, further comprising positioning a guide in the opening of the housing, wherein inserting the biopsy needle through the opening comprises inserting the biopsy needle through the guide, wherein the guide comprises two or fewer openings configured to accept the insertion member.

21. The method of claim 16, further comprising:
- inserting, a radioactive member through the opening of the housing into the object to the depth determined using the imaging information from the first detector unit and the second detector unit;
- detecting a location of the radioactive member in the object using the imaging unit;
- comparing the location of the radioactive member with the region of interest based on the location of the radioactive member; and
- adjusting the depth determined using the imaging information from the first detector unit and the second detector unit if the location of the radioactive member differs from the region of interest.

* * * * *